(12) United States Patent
Shen

(10) Patent No.: US 11,116,507 B2
(45) Date of Patent: Sep. 14, 2021

(54) END EFFECTOR ASSEMBLY FOR A CIRCULAR STAPLER APPARATUS

(71) Applicant: Covidien LP, Mansfield, MA (US)

(72) Inventor: Dongming Shen, Shanghai (CN)

(73) Assignee: Covidien LP, Mansfield, MA (US)

( * ) Notice: Subject to any disclaimer, the term of this patent is extended or adjusted under 35 U.S.C. 154(b) by 30 days.

(21) Appl. No.: 16/486,051

(22) PCT Filed: Mar. 9, 2017

(86) PCT No.: PCT/CN2017/076115
§ 371 (c)(1),
(2) Date: Aug. 14, 2019

(87) PCT Pub. No.: WO2018/161301
PCT Pub. Date: Sep. 13, 2018

(65) Prior Publication Data
US 2020/0054338 A1    Feb. 20, 2020

(51) Int. Cl.
*A61B 17/068* (2006.01)
*A61B 17/115* (2006.01)
(Continued)

(52) U.S. Cl.
CPC . *A61B 17/1155* (2013.01); *A61B 2017/00473* (2013.01); *A61B 2017/07257* (2013.01);
(Continued)

(58) Field of Classification Search
CPC .................. A61B 17/1155; A61B 2017/07257
See application file for complete search history.

(56) References Cited

U.S. PATENT DOCUMENTS 3,193,165 A    7/1965  Akhalaya et al.
3,388,847 A    6/1968  Kasulin et al.
(Continued)

FOREIGN PATENT DOCUMENTS

CA    908529 A    8/1972
CA    2805365 A1    8/2013
(Continued)

OTHER PUBLICATIONS

Supplementary European Search Report dated Oct. 5, 2020, issued in corresponding EP Appln. No. 17899956, 7 pages.

*Primary Examiner* — Andrew M Tecco
*Assistant Examiner* — Eyamindae C Jallow

(57) ABSTRACT

An end effector assembly for use with a circular stapler apparatus permits alignment of the staple forming pockets of the anvil assembly and the staples of the staple cartridge assembly regardless of the relative orientation of the components. The end effector assembly includes a cartridge housing, a staple retainer having a plurality of staples arranged in a circular array, a staple pusher at least partially disposed within the cartridge housing and configured for movement through a firing stroke to eject the staples from the staple retainer, an anvil rod configured for coupling relative to the cartridge housing, and an anvil head including at least one continuous circular staple forming pocket. The staple forming pocket is in registration with the staples for at least partial reception of the staples during the firing stroke. The staple forming pocket is configured for at least partially deforming the staples.

12 Claims, 9 Drawing Sheets

(51) Int. Cl.
*A61B 17/00* (2006.01)
*A61B 17/072* (2006.01)

(52) U.S. Cl.
CPC ............ *A61B 2017/07271* (2013.01); *A61B 2017/07285* (2013.01); *A61B 2017/1157* (2013.01)

(56) References Cited

U.S. PATENT DOCUMENTS

| | | |
|---|---|---|
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |

(56) References Cited

U.S. PATENT DOCUMENTS

| | | |
|---|---|---|
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |

(56) References Cited

U.S. PATENT DOCUMENTS

| | | |
|---|---|---|
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,405 B2 | 2/2012 | Milliman |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,733,611 B2 | 5/2014 | Milliman |
| 9,022,274 B2* | 5/2015 | Penna .................. A61B 17/115 227/179.1 |
| 9,750,503 B2* | 9/2017 | Milliman ............ A61B 17/1155 |
| 2003/0111507 A1 | 6/2003 | Nunez |
| 2004/0073090 A1 | 4/2004 | Butler et al. |
| 2005/0023325 A1* | 2/2005 | Gresham .............. A61B 17/115 227/176.1 |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0011916 A1 | 1/2011 | Levine |
| 2011/0095068 A1* | 4/2011 | Patel .................... A61B 17/072 227/180.1 |
| 2011/0095070 A1* | 4/2011 | Patel .................... A61B 17/105 227/181.1 |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0147432 A1 | 6/2011 | Heinrich et al. |
| 2011/0192882 A1 | 8/2011 | Hess et al. |
| 2012/0145755 A1 | 6/2012 | Kahn |
| 2012/0168487 A1* | 7/2012 | Holsten ............ A61B 17/07207 227/176.1 |

(56) References Cited

U.S. PATENT DOCUMENTS

| | | |
|---|---|---|
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0026209 A1* | 1/2013 | Mozdzierz ......... A61B 17/1155 227/180.1 |
| 2013/0032628 A1 | 2/2013 | Li et al. |
| 2013/0056516 A1 | 3/2013 | Viola |
| 2013/0060258 A1 | 3/2013 | Giacomantonio |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181035 A1 | 7/2013 | Milliman |
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |
| 2014/0110457 A1 | 4/2014 | Zhang |
| 2015/0014393 A1* | 1/2015 | Milliman ........... A61B 17/1155 227/180.1 |
| 2015/0115015 A1* | 4/2015 | Prescott ........... A61B 17/07292 227/179.1 |
| 2015/0351769 A1* | 12/2015 | Lee ................... A61B 17/1155 227/179.1 |
| 2016/0030046 A1* | 2/2016 | Williams ............ A61B 17/072 227/181.1 |
| 2016/0106418 A1* | 4/2016 | Shi ..................... A61B 17/068 227/175.2 |
| 2016/0143641 A1 | 5/2016 | Sapienza et al. |
| 2016/0157856 A1 | 6/2016 | Williams et al. |
| 2016/0174988 A1 | 6/2016 | D'Agostino et al. |
| 2016/0302792 A1 | 10/2016 | Motai |
| 2019/0008518 A1* | 1/2019 | Sgroi, Jr. ........... A61B 17/1155 |

FOREIGN PATENT DOCUMENTS

| | | |
|---|---|---|
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2138118 A2 | 12/2009 |
| EP | 2168510 A1 | 3/2010 |
| EP | 2238926 A2 | 10/2010 |
| EP | 2524656 A2 | 11/2012 |
| EP | 2649949 A1 | 10/2013 |
| EP | 2873380 A1 | 5/2015 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 98/35614 A1 | 8/1998 |
| WO | 0154594 A1 | 8/2001 |
| WO | 2008107918 A1 | 9/2008 |

* cited by examiner

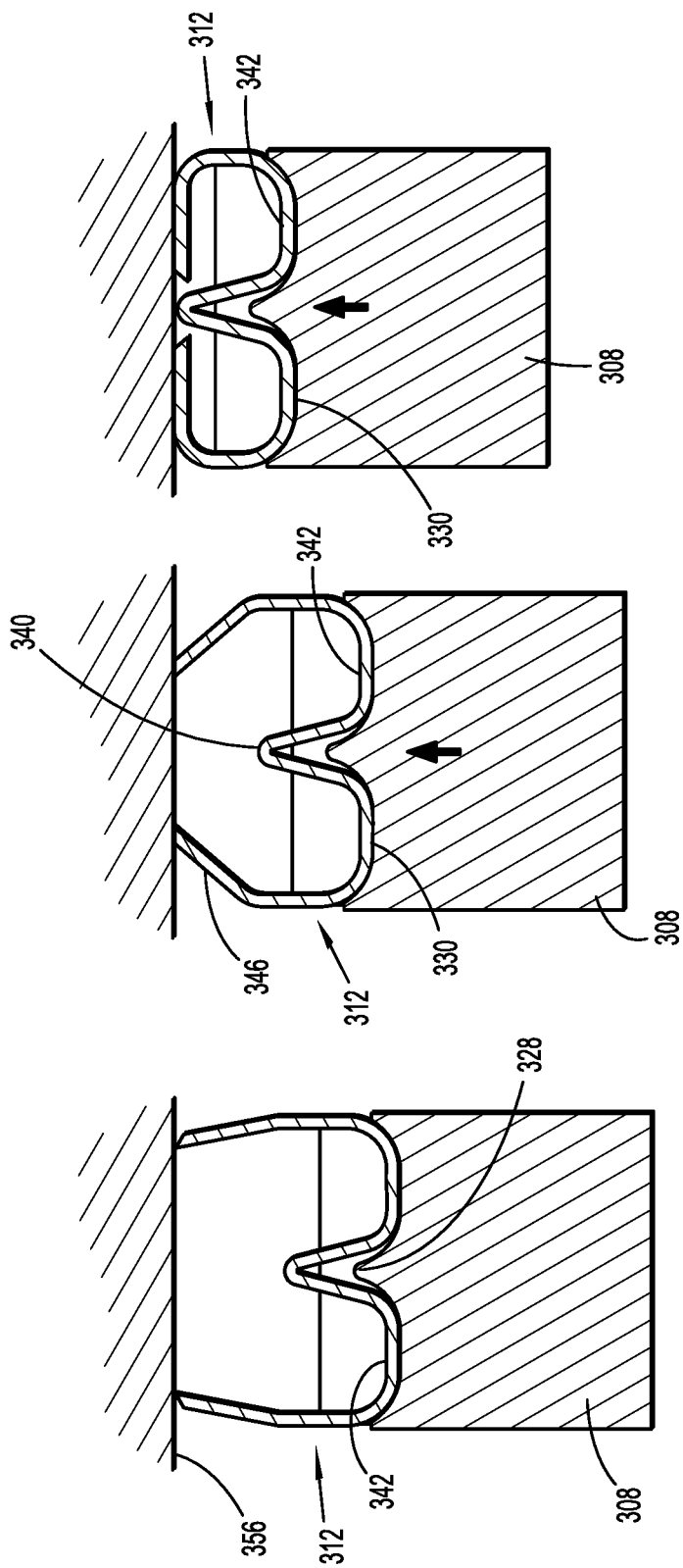

END EFFECTOR ASSEMBLY FOR A CIRCULAR STAPLER APPARATUS

CROSS-REFERENCE TO RELATED APPLICATIONS

This application is a U.S. National Stage Application filed under 35 U.S.C. § 371(a) which claims the benefit of and priority to International Patent Application Serial No. PCT/CN2017/076115, filed Mar. 9, 2017, the entire disclosure of which is incorporated by reference herein.

BACKGROUND

1. Technical Field

The present disclosure relates to a surgical stapler apparatus and, more particularly, relates to an end effector assembly for a circular stapler apparatus. The present disclosure further relates to an end effector assembly including staple cartridge and anvil mechanisms incorporating features permitting firing of the staples without requiring indexing of the anvil mechanism with the staple cartridge mechanism.

2. Discussion of Related Art

Circular stapler instruments are utilized by clinicians to apply one or more surgical fasteners, e.g., staples or two-part staples, to body tissue for the purpose of joining together segments of body tissue and/or for the creation of an anastomosis. Circular stapler instruments generally include an annular staple cartridge assembly supporting a plurality of annular rows of staples, an annular anvil assembly operatively associated with the staple cartridge assembly and having individual staple forming pockets for providing a surface against which the staples are formed, and an annular blade for cutting tissue.

During a typical fastening procedure, the anvil assembly is separated from the stapler instrument and is positioned within one segment of body tissue. The stapler instrument is positioned in an adjacent segment of body tissue. The anvil assembly is then attached to the cartridge assembly and the stapler instrument is maneuvered to approximate the anvil assembly with the cartridge assembly to clamp together the segments of body tissue. Typically, the anvil rod of the anvil assembly and the cartridge shell or housing of the cartridge assembly incorporate structure such as external and internal splines, respectively, to ensure the individual staple forming pockets of the anvil assembly are in direct alignment with the staples of the cartridge assembly for proper staple formation during the firing sequence. Unfortunately, misalignment of the splines may occur, particularly, in high-speed auto clamping procedures. Such misalignment may potentially damage the splines, which often results in off-axis staple formation and accompanying defects in tissue connection or anastomosis.

SUMMARY

Accordingly, the present disclosure is directed to an end effector assembly for a circular stapler instrument, which permits automatic alignment of the staple forming pockets of the anvil assembly and the staples of the staple cartridge assembly regardless of the relative orientation of the components. In one embodiment, an end effector assembly for use with a circular stapler apparatus is disclosed. The end effector assembly includes a cartridge housing defining a central housing axis, a staple retainer disposed within the cartridge housing and having a plurality of staples arranged in a circular array about the central housing axis, a staple pusher at least partially disposed within the cartridge housing and configured for movement through a firing stroke to eject the staples from the staple retainer, an anvil rod configured for coupling relative to the cartridge housing, and an anvil head including at least one continuous circular staple forming pocket. The staple forming pocket is in registration with the staples for at least partial reception of the staples during the firing stroke. The staple forming pocket is configured for at least partially deforming the staples.

In embodiments, the cartridge housing includes an inner anvil receptacle configured to receive the anvil rod to mount the anvil rod relative to the cartridge housing. In some embodiments, the inner anvil receptacle defines a cylindrical section having a continuous inner surface devoid of splines. In certain embodiments, the anvil rod is also devoid of splines.

In embodiments, the staple pusher includes a plurality of pusher fingers. Each pusher finger is configured to engage an individual staple to eject the individual staple from the staple retainer to deform the individual staple within the staple forming pocket. In some embodiments, the pusher fingers are arranged in a circular array corresponding to the circular array of the staples.

In certain embodiments, the staple retainer includes first and second sets of a plurality of staples concentrically arranged with respect to the central housing axis and the anvil head includes first and second continuous circular staple forming pockets concentrically arranged with respect to the central housing axis. The first and second continuous staple forming pockets are in registration with the staples of the respective first and second sets of the staples for at least partial reception and deformation during the firing stroke. In embodiments, the staple retainer includes a third set of a plurality of staples concentrically arranged with respect to the central housing axis and the anvil head includes a third continuous circular staple forming pocket concentrically arranged with respect to the central housing axis, and in registration with the staples of the third set of the staples for at least partial reception and deformation during the firing stroke.

In some embodiments, each pusher finger is configured to extend along a central pusher axis in parallel relation with the central housing axis. In certain embodiments, each pusher finger includes two concavities on opposed sides of the central pusher axis. In certain embodiments, each staple includes a staple backspan and opposed legs depending from the staple backspan. Each staple defines a staple axis extending along a length of the staple. The staple backspans of each staple have two convexities on opposed sides of the staple axis. The concavities of each pusher finger are configured to engage respective convexities of the staples during the firing stroke of the staple pusher. In some embodiments, each opposed leg of the staples has an oblique remote end segment. The oblique remote end segment extends radially inwardly relative to the staple axis and is configured to facilitate deformation of the opposed legs during the firing stroke.

The present disclosure provides significant advantages over known circular stapler instruments. The staple cartridge mechanism of the end effector assembly includes a cartridge housing incorporating a staple pusher capable of movement through a firing stroke to eject and form the staples against an anvil head regardless of the orientation of the anvil head relative to the staple pusher. Specifically, the anvil head includes at least one continuous circular staple forming pocket which is in registration with the staples and with a circular array of individual pusher fingers of the staple pusher. Thus, the need to incorporate alignment features such as indexing splines on the anvil rod and within the cartridge housing to align the staple forming pockets and the staples is eliminated along with the associated drawbacks hereinabove described.

Other features and advantages of the present disclosure will be better appreciated by the following description.

BRIEF DESCRIPTION OF THE DRAWINGS

Various aspects of the present disclosure are described hereinbelow with reference to the drawings, which are incorporated in and constitute a part of this specification, wherein:

FIGS. 14-16 are views illustrating a sequence of formation of a staple with the single continuous staple forming pocket.

DETAILED DESCRIPTION

Figure 1:
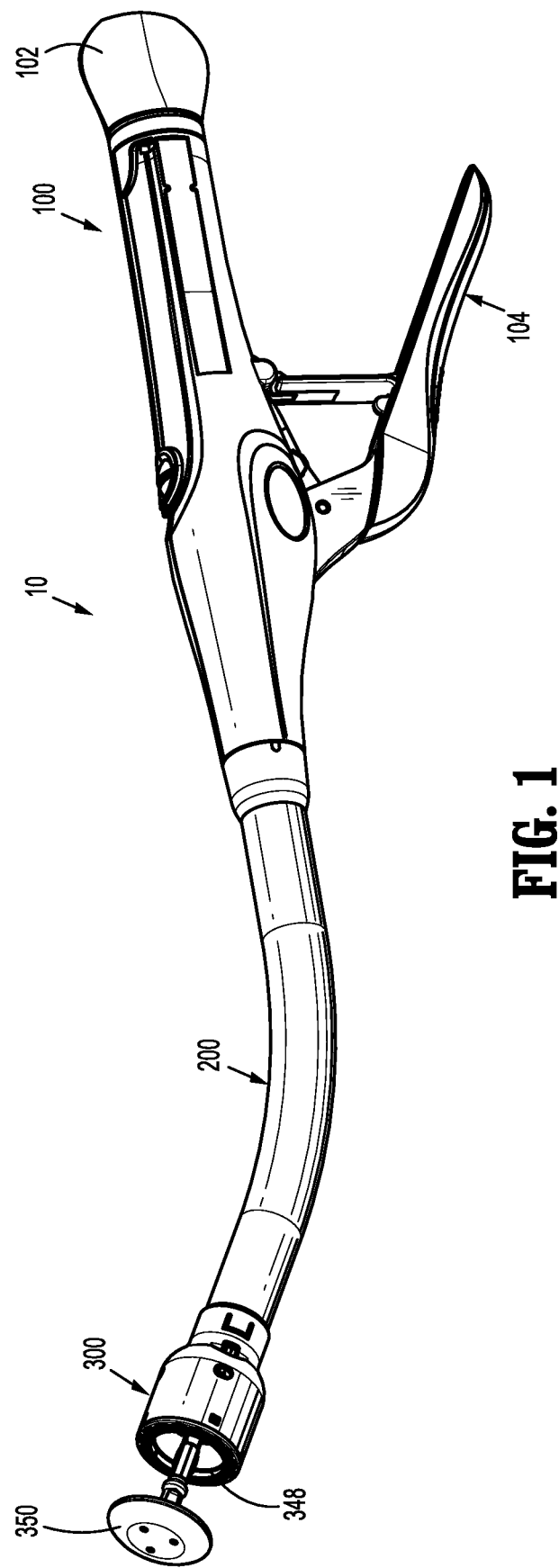
FIG. 1 is a perspective view of an exemplary circular stapler apparatus illustrating an end effector assembly including a staple cartridge mechanism and an anvil mechanism in accordance with the present disclosure.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to that portion of the assembly or component thereof that is closest to the clinician and the term "distal" refers to that portion of the device or component thereof that is farthest from the clinician.

Referring initially to FIG. 1, a circular or end-to-end stapler apparatus is illustrated, and is generally designated as reference numeral 10. The circular stapler apparatus 10 may be adapted for reuse or alternatively is disposable after a single use. The circular stapler apparatus 10 includes a handle assembly 100, an elongate body 200 extending from the handle assembly 100, and an end effector assembly 300. The end effector assembly 300 may be provided as a removable and replaceable assembly that is releasably secured relative to the elongate body 200. Alternatively, the end effector assembly 300 may be permanently secured to the elongate body 200. The handle assembly 100 includes a rotatable advancing approximator 102 and a pivotable trigger member 104 that are operatively coupled to mechanisms supported within the elongate body 200 to respectively effectuate approximation and firing of the circular stapler apparatus 10. In some embodiments, the elongate body 200 has a linear shape along at least a portion of its length, and in other embodiments, the elongate body 200 has a curved shape along at least a portion of its length.

For a detailed discussion of the construction and operation of an exemplary circular stapler apparatus, reference may be made to commonly assigned U.S. Patent Publication No. 20150014393 to Milliman, the entire contents of which is incorporated herein by reference.

Figure 2:
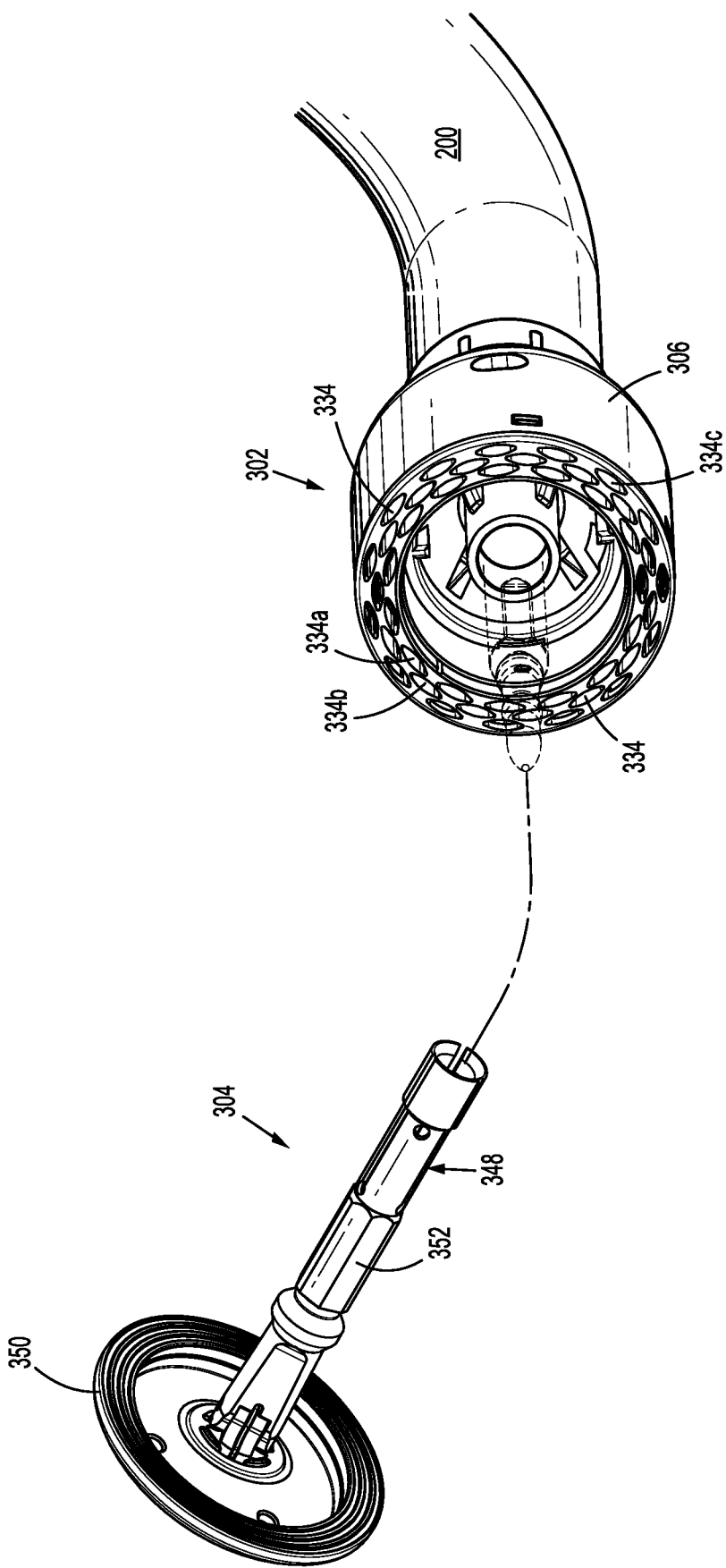
FIG. 2 is a perspective view of the end effector assembly illustrating the anvil mechanism separated from the staple cartridge mechanism.
Figure 3:
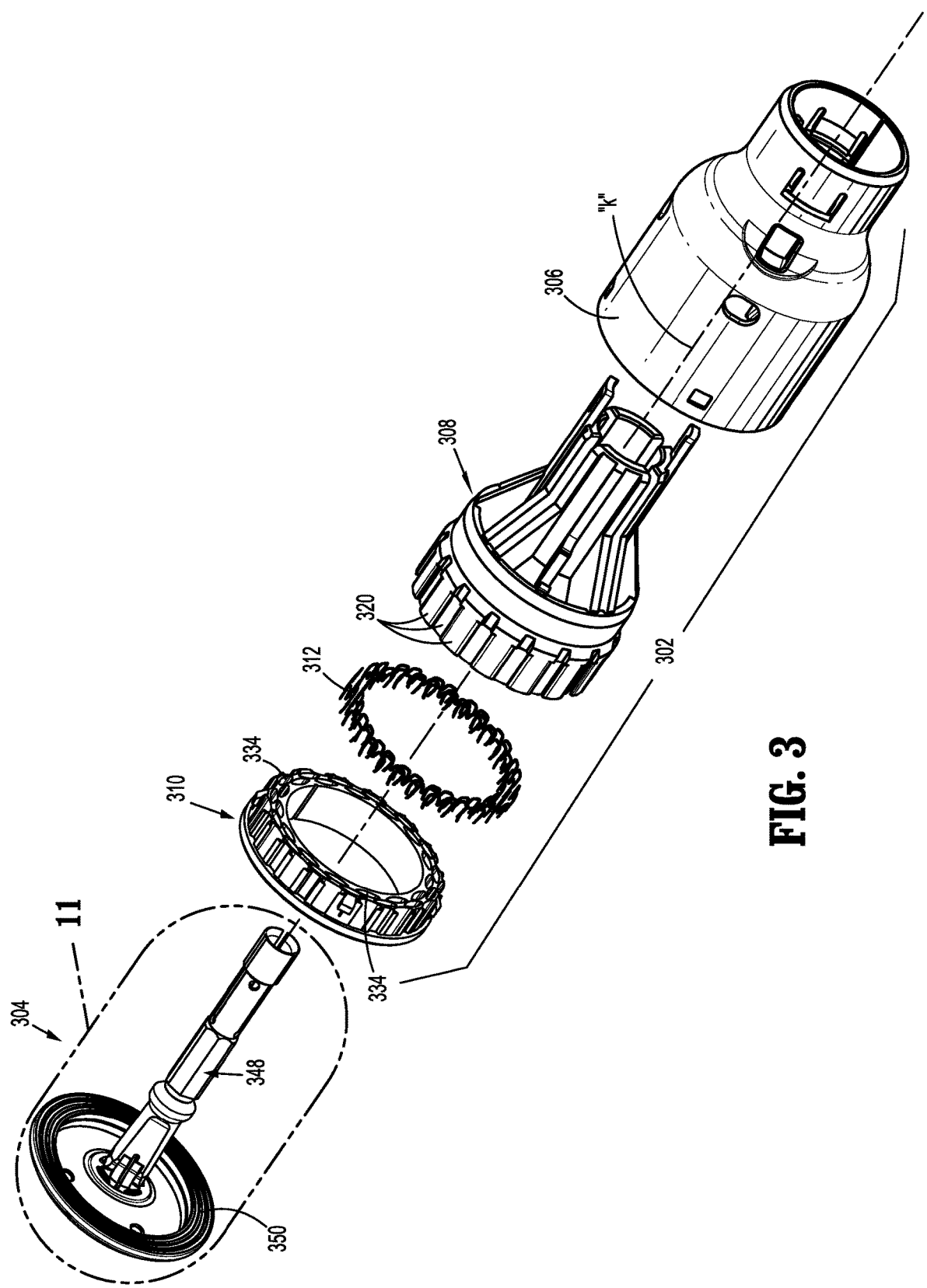
FIG. 3 is an exploded perspective view of the end effector assembly.

With reference to FIGS. 2-3, the end effector assembly 300 includes a staple cartridge mechanism 302 and an anvil mechanism 304 which is releasably mountable to the staple cartridge mechanism 302. The staple cartridge mechanism 302 includes a cartridge housing 306, a pusher 308, a staple retainer 310 and a plurality of staples 312 contained within the staple retainer 310. The staple cartridge mechanism 302 may house a plurality of additional components that do not form part of this disclosure and are not shown or described further herein. In embodiments, the staple cartridge mechanism 302 and/or the anvil mechanism 304 of the end effector assembly 300 may be replaced and the circular stapler apparatus 10 may be reused. In embodiments, the end effector assembly 300 includes a knife assembly (not shown) adapted to cut tissue.

Figure 4:
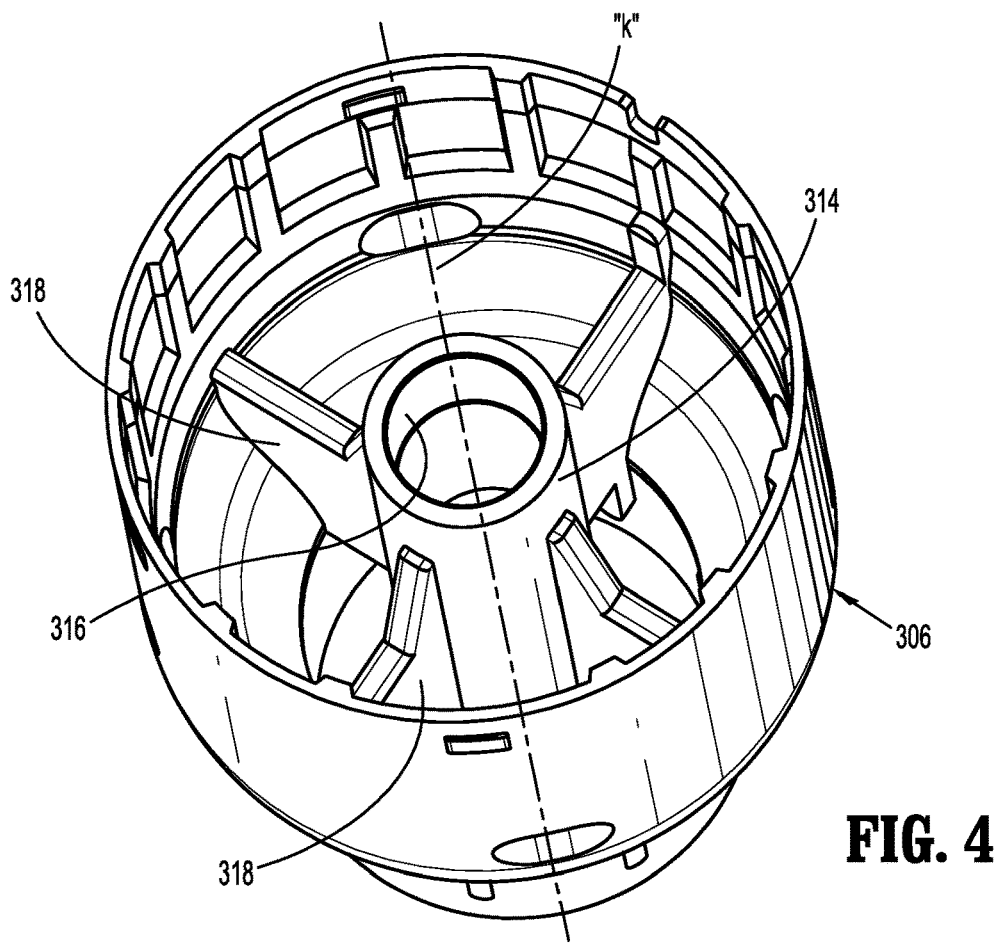
FIG. 4 is a top perspective view of the cartridge housing of the staple cartridge mechanism.

Referring now to FIG. 4, in conjunction with FIG. 3, the cartridge housing 306 is the outer shell which accommodates the remaining components of the staple cartridge mechanism 302. The cartridge housing 306 defines a central longitudinal housing axis "k". Disposed within the interior of the cartridge housing 306 in general alignment with the central housing axis "k" is an inner anvil receptacle 314. The inner anvil receptacle 314 is generally cylindrical in configuration and defines an internal surface 316 devoid of irregularities, e.g., splines or the like, which are typically present in conventional circular stapler apparatuses. In embodiments, the internal surface 316 is smooth and continuous. The inner anvil receptacle 314 is mounted within the cartridge housing 306 by the inner ribs 318 extending outwardly from the inner receptacle 314 and coupled to the wall of the cartridge housing 306. The inner anvil receptacle 314 may accommodate a trocar 400 (FIG. 2) which extends through the anvil receptacle 314 and is operatively coupled to the rotatable advancing approximator 102 of the handle assembly 100. The trocar 400 assists in mounting the anvil mechanism 304 relative to the staple cartridge mechanism 302. The cartridge housing 306 including the inner anvil receptacle 314 and the ribs 318 may be monolithically formed of a suitable polymeric material.

Figure 5:
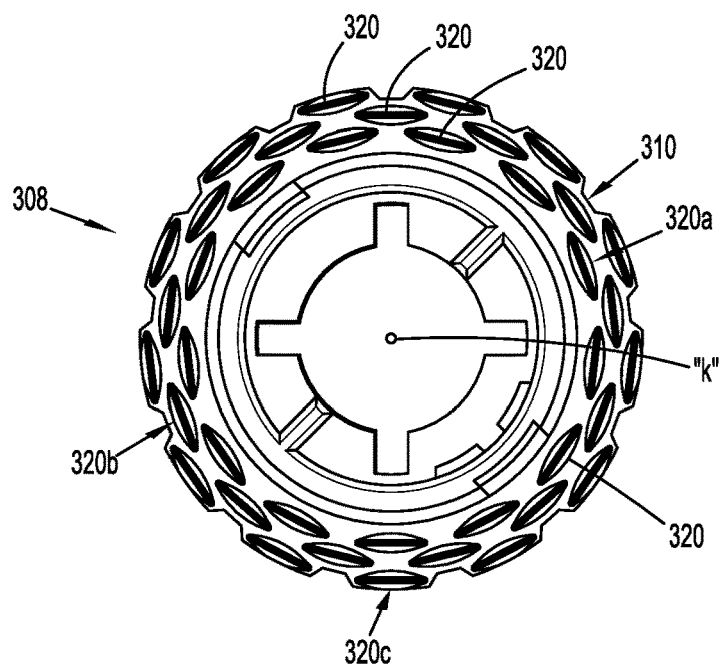
FIG. 5 is a top plan view of the staple pusher of the staple cartridge mechanism.

With reference now to FIGS. 3 and 5, the pusher 308 is at least partially received within the cartridge housing 306. The pusher 308 is coupled to the pivotable trigger member 104 whereby actuation of the trigger member 104 causes the pusher 308 to undergo a firing stroke. The pusher 308 includes at least one annular, e.g., circular, array of individual pusher fingers 320 (FIG. 5) coaxially arranged with respect to the central housing axis "k". In embodiments, the pusher assembly includes first (inner), second (middle) and third (outer) circular arrays 320a, 320b, 320c of individual pusher fingers 320 concentrically or coaxially arranged about the central housing axis "k".

Figure 6:
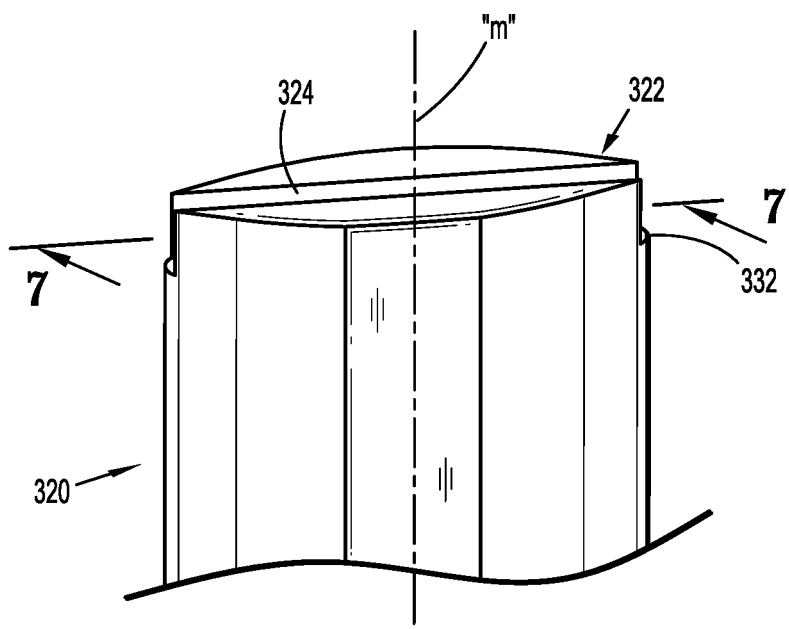
FIG. 6 is a perspective view of an individual pusher finger of the staple pusher.
Figure 7:
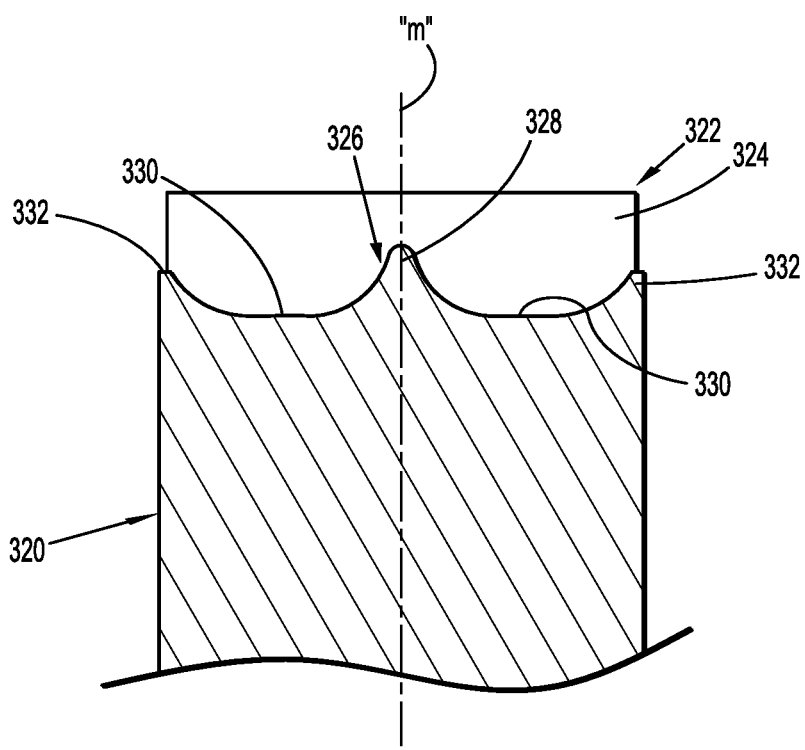
FIG. 7 is a cross-sectional view taken along the lines 7-7 of FIG. 6 illustrating the dual concavities of the pusher finger.

FIGS. 6-7 illustrate an individual pusher finger 320 of the circular arrays 320a, 320b, 320c. Each individual pusher finger 320 extends along a central pusher axis "m" in parallel relation with the central housing axis "k". The individual pusher fingers 320 each include a distal pusher end 322 defining a recess 324 for at least partial reception of an individual staple 312. Within each recess 324 is a pusher face 326 having a projection 328 in alignment with the central pusher axis "m" and two concavities 330 on opposed sides of the projection 326 and contiguous therewith. The concavities 330 extend to outer edges 332 of the pusher finger 320. The projection 326, concavities 330 and outer edges 332 of each pusher finger 320 cooperate to deform an individual staple 312.

Figure 8:
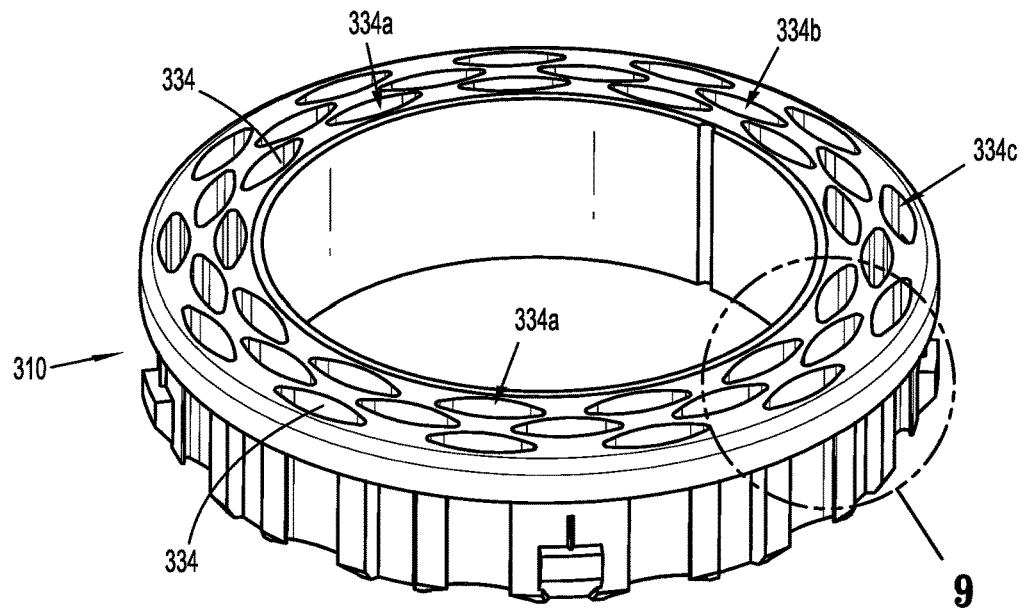
FIG. 8 is a perspective view of the staple retainer.
Figure 9:
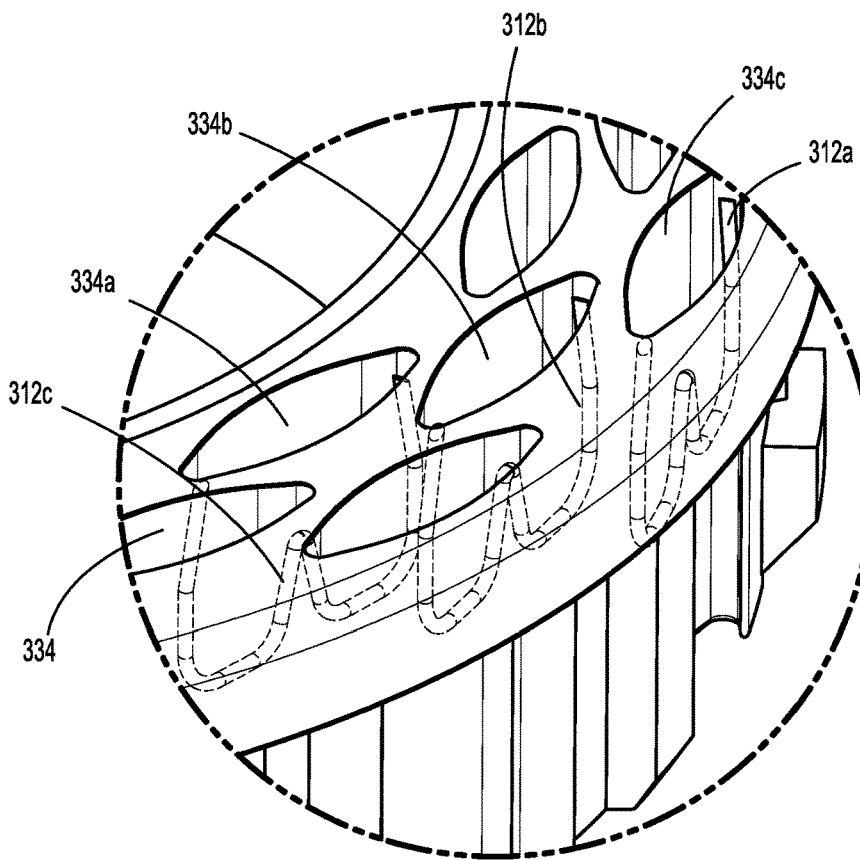
FIG. 9 is an enlarged isolated view of the area of detail identified in FIG. 8.

Referring to FIGS. 8-9, the staple retainer 310 is generally annular in configuration and is at least partially received within the cartridge housing 306. The staple retainer 310 includes at least one annular, e.g., circular, array of staple receiving openings 334. In embodiments, the staple retainer 310 includes first (inner), second (middle) and third (outer) circular arrays 334a, 334b, 334c of individual openings 334 concentrically or coaxially arranged about the central housing axis "k" and in registration with the first, second and third arrays 320a, 320b, 320c of the pusher fingers 320. (FIG. 5) The staple receiving openings 334 each accommodate an individual staple 312 thus presenting first (inner), second (middle) and third (outer) circular arrays 312a, 312b, 312c of staples 312 which are also in registration with the first, second and third circular arrays 320a, 320b, 320c of pusher fingers 320.

Figure 10:
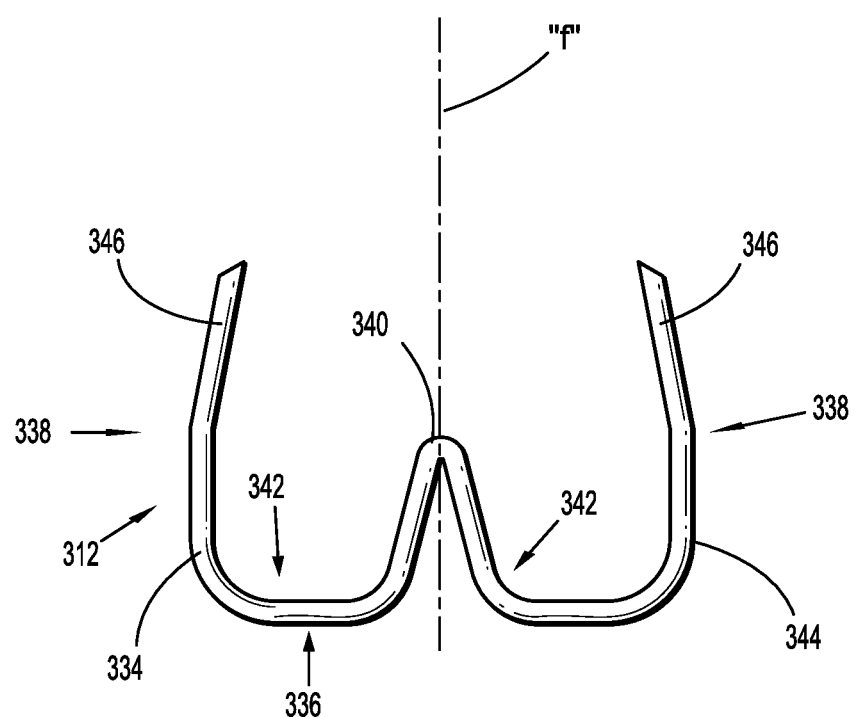
FIG. 10 is a side elevation view of an individual surgical staple of the staple cartridge mechanism.

Referring now to FIG. 10, each individual staple 312 of the circular arrays of staples 312 will be discussed. Each staple 312 includes a staple backspan 336 and opposed legs 338 depending from the staple backspan 336. The staples 312 each define a staple axis "f" extending along the length of the staple 312 and being parallel, or in alignment with, the central pusher axis "m". The staple backspan 336 of each staple 312 defines an inverted vertex or projection 340 in alignment with the staple axis "f" and two convexities 342 on opposed sides of the inverted vertex 340 and contiguous therewith. Each opposed 338 leg of the staples 312 has a linear segment 344 extending contiguously from the backspan 336 and an oblique remote end segment 346 extending from the linear segment 344 and depending radially inwardly relative to the staple axis "f". The oblique remote end segments 346 are configured to facilitate deformation of the opposed legs 338 during the firing stroke.

Figure 11:
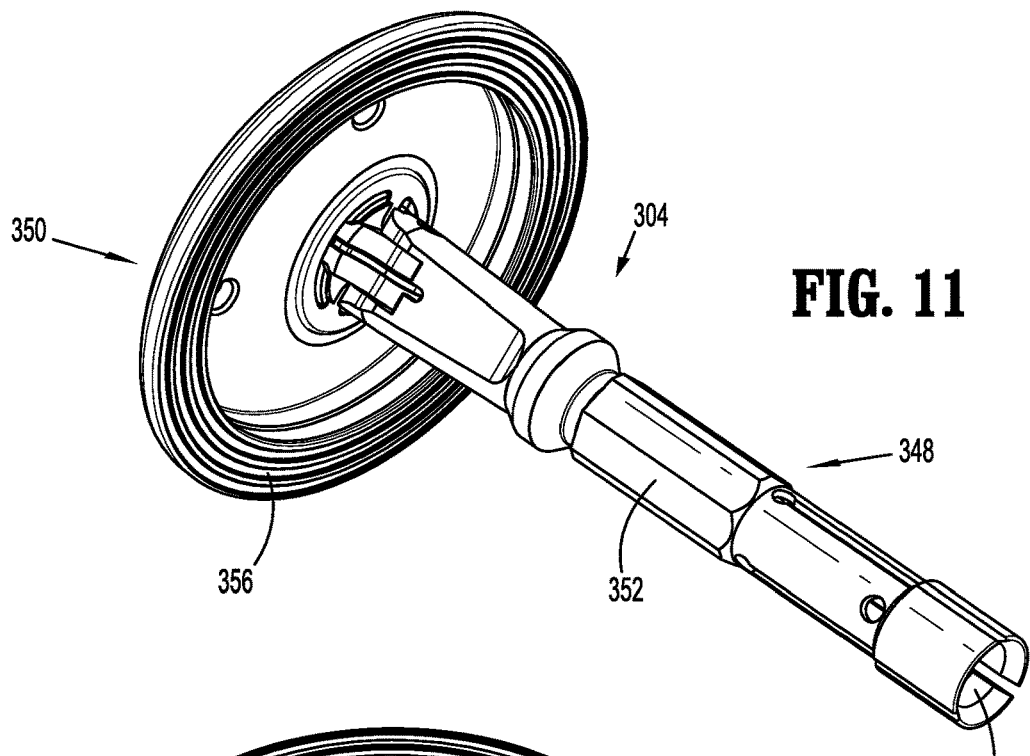
FIG. 11 is perspective view of the anvil mechanism of the end effector assembly.
Figure 12:
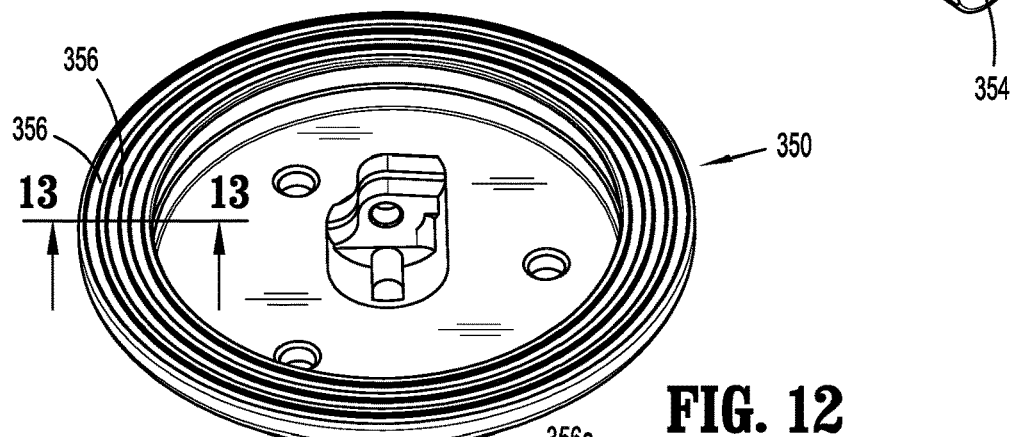
FIG. 12 is a top perspective view of the anvil head of the anvil mechanism illustrating the continuous staple forming pockets of the anvil head.
Figure 13:
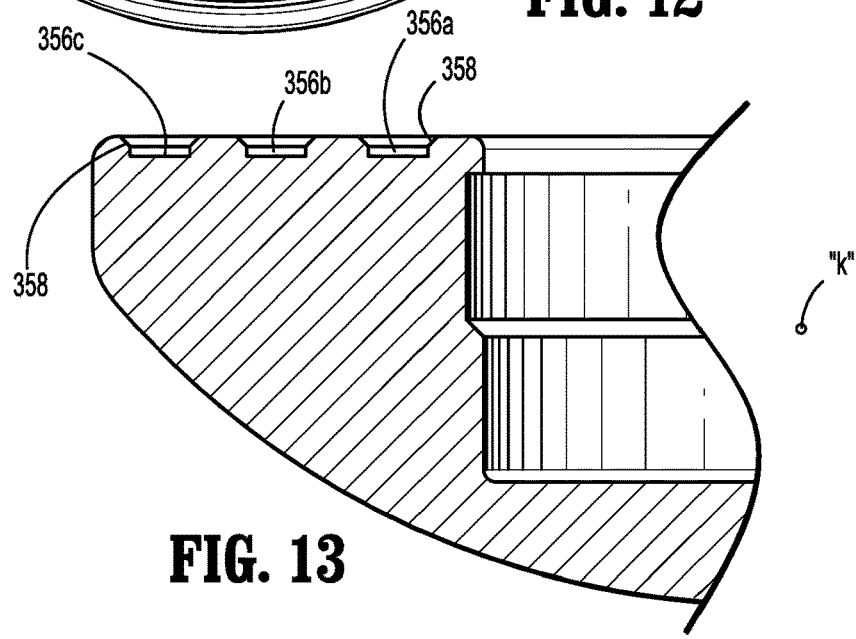
FIG. 13 is an enlarged cross-sectional view taken along the lines 13-13 of FIG. 12.

Referring now to FIGS. 11-13, the anvil mechanism 304 of the end effector assembly 300 will be discussed. The anvil mechanism 304 includes a central anvil rod 348 and an anvil head 350 coupled to the central anvil rod 348. In embodiments, the anvil head 350 may be pivotally mounted to the anvil rod 348. The anvil rod 348 may include a plurality of intersecting planar surfaces 352 configured to facilitate grasping engagement by forceps instrument or the like. However, unlike conventional anvil assemblies, the anvil rod 348 is devoid of any spline structure typically utilized to align individual staple forming pockets of the anvil head with the staple retainer. In fact, the anvil rod 348 is completely devoid of any structure which would otherwise rotationally align the anvil head 350 with the staple retainer 310. In embodiments, the anvil rod 348 may be capable of rotating within the inner anvil receptacle 314 of the cartridge housing 306 when the components are coupled. The anvil rod 348 includes an opening 354 for reception of the trocar 400 (FIG. 2) and includes cooperating structure to releasably secure the anvil mechanism 304 relative to the trocar 400 and the staple cartridge mechanism 302.

The anvil head 350 includes at least one continuous annular, e.g., circular, staple forming pocket 356 coaxially arranged about the central housing axis "k" when the anvil mechanism is mounted to the cartridge housing 306. The staple receiver pocket 356 is in registration with one of the circular array 312a, 312b, 312c of staples 312 for at least partial reception of the staples 312 during the firing stroke to deform at least the opposed legs 338 of the staples 312. In embodiments, the anvil head 350 includes first (inner), second (middle) and third (outer) continuous circular staple forming pockets 356a, 356b, 356c (FIG. 13) concentrically arranged with respect to the central housing axis "k". The first, second and third staple forming pockets 356a, 356b, 356c are in registration with the respective staples 312 of the respective first, second and third circular arrays 312a, 312b, 312c of the staples 312 within the staple retainer 310. In embodiments, each staple forming pocket 356a, 356b, 356c includes opposed chamfered or cam surfaces 358 to assist in guiding or retaining the opposed legs 338 of the staples 312 into the staple forming pockets 356.

The use of the end effector assembly 300 in conjunction with an anastomosis procedure performed with the circular stapler apparatus 10 will be discussed. The anvil mechanism 304 is positioned within a first tubular organ and the organ may be secured about the anvil head 350 with a purse string suture or the like. The circular stapler apparatus 10 with mounted staple cartridge mechanism 302 is positioned within a second tubular organ. The anvil rod 348 is mounted to the inner anvil receptacle 314 of the cartridge housing 306 by insertion of the anvil rod 348 within the inner anvil receptacle 314. In embodiments, the opening 354 of the anvil rod 348 also may receive the trocar 400 (FIG. 2), and may be releasably secured to the trocar 400 via cooperating structure between the two components. As discussed hereinabove, there are no indexing splines associated with the anvil rod 348 or the cartridge housing 306 due at least in part to the circular arrays 320a, 320b, 320c of the pusher fingers 320 and the continuous circular staple forming pockets 356a, 356b, 356c. Specifically, the anvil rod 348 resides within the inner anvil receptacle 314 unconstrained from rotational movement. The anvil head 350 is approximated relative to the cartridge housing 306 through manipulation of the approximator 102 of the handle assembly 100. The trigger 104 is actuated to cause the pusher 308 to undergo a firing stroke. During advancement of the pusher 308, the first, second and third circular arrays 320a, 320b, 320c of pusher fingers 320 traverse the corresponding first, second and third arrays 334a, 334b, 334c of the staple retainer 310 to eject the first, second and third circular arrays 312a, 312b, 312c of staples 312 from the staple retainer 310. The ejected first, second and third arrays 312a, 312b, 312c of the staples 312 are cooperatively received within the first, second and third continuous staple forming pockets 356a, 356b, 356c where they are deformed to join together ends of the tubular organs.

FIGS. 14-16 illustrate a sequence of deformation of an individual staple within a staple forming pocket 356 during the firing stroke. As shown, the individual pusher 308 engages the staple backspans 336 of the staple 312 with the convexities 342 received within the concavities 330 of the pusher face 326 and the projection 328 of the pusher face 326 received within the interior of the inverted vertex 340 of the staple 312. Upon further advancement of the individual pusher through the firing stroke as depicted in FIGS. 14-15, the oblique remote end segment 346 engages the staple forming pocket 356 and deforms (e.g. at the points of intersection with the linear segments 344) to form a general "B" shape joining together the tubular organs.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed is:

1. An end effector assembly for use with a circular stapler apparatus, which comprises:
    a cartridge housing defining a central housing axis;
    a staple retainer disposed within the cartridge housing, the staple retainer including a plurality of staples arranged in at least one circular array about the central housing axis;
    a staple pusher at least partially disposed within the cartridge housing, the staple pusher configured for movement through a firing stroke to eject the staples from the staple retainer;
    an anvil rod configured for coupling relative to the cartridge housing; and
    an anvil head including at least one continuous circular staple forming pocket, the staple forming pocket in registration with the plurality of staples in one circular array of the at least one circular array for at least partial reception of the plurality of staples in the one circular array during the firing stroke, the staple forming pocket configured for at least partially deforming the staples.

2. The end effector assembly according to claim 1 wherein the cartridge housing includes an inner anvil receptacle configured to receive the anvil rod to mount the anvil rod relative to the cartridge housing.

3. The end effector assembly according to claim 2 wherein the inner anvil receptacle defines a cylindrical section having a continuous inner surface devoid of splines.

4. The end effector assembly according to claim 3 wherein the anvil rod is devoid of splines.

5. The end effector assembly according to claim 1 wherein the staple pusher includes a plurality of pusher fingers, each pusher finger configured to engage an individual staple to eject the individual staple from the staple retainer to deform the individual staple within the staple forming pocket.

6. The end effector assembly according to claim 5 wherein the pusher fingers are arranged in a circular array corresponding to the circular array of the staples.

7. The end effector assembly according to claim 6 wherein each pusher finger is configured to extend along a central pusher axis in parallel relation with the central housing axis.

8. The end effector assembly according to claim 7 wherein each pusher finger includes two concavities on opposed sides of the central pusher axis.

9. The end effector assembly according to claim 8 wherein each staple includes a staple backspan and opposed legs depending from the staple backspan, each staple defining a staple axis extending along a length of the staple, the staple backspans of each staple having two convexities on opposed sides of the staple axis, the concavities of each pusher finger configured to engage respective convexities of the staples during the firing stroke of the staple pusher.

10. The end effector assembly according to claim 9 wherein each opposed leg of the staples have an oblique remote end segment, the oblique remote end segment extending radially inwardly relative to the staple axis and configured to facilitate deformation of the opposed legs during the firing stroke.

11. The end effector assembly according to claim 5 wherein the staple retainer includes first and second sets of a plurality of staples concentrically arranged with respect to the central housing axis and wherein the anvil head including first and second continuous circular staple forming pockets concentrically arranged with respect to the central housing axis, the first and second continuous staple forming pockets in registration with the staples of the respective first and second sets of the staples for at least partial reception and deformation during the firing stroke.

12. The end effector assembly according to claim 11 wherein the staple retainer includes a third set of a plurality of staples concentrically arranged with respect to the central housing axis and wherein the anvil head including a third continuous circular staple forming pockets concentrically arranged with respect to the central housing axis, and being in registration with the staples of the third set of the staples for at least partial reception and deformation during the firing stroke.

* * * * *